United States Patent [19]

Lemonnier

[11] Patent Number: 4,912,037
[45] Date of Patent: Mar. 27, 1990

[54] CONTAINER FOR MICRO-ORGANISM CULTURE MEDIA

[75] Inventor: Jean Lemonnier, Le Vesinet, France

[73] Assignee: Millipore S.A., St. Quentin en Yvelines Cedex, France

[21] Appl. No.: 109,977

[22] Filed: Oct. 19, 1987

[30] Foreign Application Priority Data

Oct. 20, 1986 [FR] France .................... 86 14551

[51] Int. Cl.⁴ .................... C12Q 1/04; C12M 1/22
[52] U.S. Cl. .................... 435/34; 435/30; 435/29; 435/31; 435/292; 435/294; 435/297; 435/298; 435/299; 435/301
[58] Field of Search ............ 435/30, 34, 297, 298, 435/299, 300, 301, 31, 32, 33, 292, 293, 294, 297

[56] References Cited

U.S. PATENT DOCUMENTS 3,630,849 12/1971 Land et al. .................... 195/139
4,326,028 4/1982 Brown .................... 435/32
4,598,050 7/1986 Brown .................... 435/298

FOREIGN PATENT DOCUMENTS 0171174 2/1986 European Pat. Off.

Primary Examiner—Robert J. Warden
Assistant Examiner—Toni R. Scheiner
Attorney, Agent, or Firm—Andrew T. Karnakis; Paul J. Cook

[57] ABSTRACT

A container for one or more micro-organism culture mediums has a substantially cylindrical or frustoconical casing open at both ends. A transverse perforated support grid is joined to an inside wall of the casing at its circular edge. A base is fitted to a lower end of the casing and a lid is fitted in a liquid-tight manner onto the upper end of the casing. A culture medium at a raised temperature can thus be poured into the container while it is resting upside down on its lid with the base removed.

14 Claims, 2 Drawing Sheets

CONTAINER FOR MICRO-ORGANISM CULTURE MEDIA

BACKGROUND OF THE INVENTION

1. Field of the invention

The present invention concerns generally a container for culture mediums. More particularly, this invention relates to a container adapted to receive one or more culture mediums for micro-organisms, a method of filling this device with such a medium or mediums and the use of such a container for the detection of micro-organisms with a view to identifying and counting them.

2. Description of the prior art

In many industries, such as the foodstuffs, pharmaceutical and electronics industries, and in hospitals, it is essential to be able to evaluate the degree to which certain products or surfaces are contaminated by micro-organisms such as bacteria, yeast and mold.

To carry our this evaluation in the case of a liquid product a sample is usually filtered through a sterile membrane filter, the membrane filter is placed on a gel nutrient culture medium in a container. This container is then incubated at an elevated temperature for a time sufficient to enable any micro-organisms that may be present in the sample to grow and multiply in the form of colonies visible to the naked eye to permit counting and identification.

One operation that is important to correctly implement this technique for counting micro-organisms on a microporous membrane filter is the placing of the filter used to separate the micro-organisms in contact with the gel culture medium. Thus the condition of the surface of the gel culture medium is an important factor in the success of the operation.

There currently exist containers referred to as Petri dishes which are made from glass or plastic. Petri dishes are usually supplied in a sterile condition for single use and are made in two parts, namely a lid and a base into which the gel nutrient medium is poured after it has been heated to liquefy it. Thereupon, the lid is merely placed over the base to cover the medium.

After the gel medium has cooled and solidified, the Petri dishes may be used or stored in a refrigerator to obtain the optimum storage conditions. The surface of the gel culture medium is then brought into contact with the microporous filter on whose top surface any micro-organisms will have been collected. Growth of the micro-organisms is then dependent on capillary action allowing media to pass through the pores of the membrane.

The use of Petri dishes has a number of disadvantages. Firstly, the surface of the gel medium may feature defects due either to an inadequate casting temperature or to excessively sudden cooling of the medium. The resulting so-called "orange peel" effect results in surface defects which compromise good contact between the culture medium and the bottom surface of the membrane filter. Good contact is essential for the micro-organisms to develop.

Also, the surface of the gel medium is deformed (i.e., not flat) at its edge because the media tends to rise by capillary action up the vertical walls of the base of the Petri dish to form a fillet. This limits the surface area of the gel that can be used and, to compensate, it is common practice to employ membrane filters with a diameter substantially less than that of the Petri dish. This results in an increase in overall size of the device and a significant volume of gel that is not used.

When the Petri dish is being filled with the gel medium there is also the risk that air bubbles may burst on the surface and, because of the viscous nature of the medium, produce craters which also compromise good contact with the membrane filter.

Because Petri dishes are filled at a raised temperature, as the culture medium cools after the lid is placed on the device, condensation occurs on the bottom of the lid. The condensate sometimes runs down onto the top of the gel medium, thereby requiring a drying operation in an oven before use. This phenomenon is accentuated when the dishes are stored in a refrigerator. Allowing the culture medium to cool without the lid exposes the surface of the gel culture medium to risks of exogenous contamination when it is stored in unsealed Petri dishes.

Finally, because of the concave shape of the surface of the medium, Petri dishes do not enable direct effective counting of any micro-organisms present on the surface by simple contact between the surface of the gel medium and the bottom surface of the membrane.

U.S. Pat. No. 4,326,028 discloses an improved Petri dish comprising a cylindrical casing to which is attached a perforated support grid and which is designed to receive in back-to-back relationship two different culture mediums. This arrangement enables observation in two compartments situated one on each side of the grid; however, the surfaces of both of the culture mediums are subject to the same disadvantages as those that affect Petri dishes as described above.

An object of the present invention is an improved container for the same application as Petri dishes but without he disadvantages mentioned above.

SUMMARY OF THE INVENTION

The invention resides in a container adapted to receive one or more culture mediums for the growth and identification of micro-organisms. In accordance with a preferred embodiment, the container includes a substantially cylindrical or frustoconical casing open at both ends, a transverse perforated support grid having a circular edge joined to an inside wall of said casing, a base and a lid which fits in a liquid-tight way onto an upper end of said casing. This arrangement allows a culture medium at a raised temperature to be poured into the container while it is resting upside down on its lid with the base removed. The container, which is preferably supplied in a sterile non-reusable form, may be made from plastic material or glass.

Filling a container of this kind with a micro-organism culture medium is accomplished by resting it upside down on its liquid-tight lid, removing the base and pouring the culture medium into the casing, which is fitted only with its lid, until the perforated support grid is immersed in the medium. The base is then replaced and the container, which may be stored in a refrigerator for subsequent use, is turned over so as to rest on its base, with the cover on its top, ready for use.

By virtue of this structure and this filling method, the surface of the nutrient medium which is brought into contact with the micro-organisms is not the top surface resulting from the pouring operation. Instead, because the container is turned over, the bottom surface of the poured medium which is directly in contact with the lid becomes the surface of interest with respect to contact with the membrane filter. Since this "contact" surface of the medium is therefore molded according to the shape of the lid, it does not have any of the defects mentioned hereinabove. In particular, this surface will not suffer from the orange peel effect, nor with it have any edge fillet or craters due to air bubbles.

Furthermore, there is no risk of condensation of water on or exogenous contamination of the surface of the nutrient medium which will be brought into contact with the micro-organisms to be detected since this surface is in direct contact with the previously sterilized lid.

Finally, by making the lid an appropriate shape, for example flat or slightly concave, it is possible to obtain a nutrient medium surface of corresponding flat or convex shape. This enables the medium surface to be applied directly by contact onto a surface to be checked for contamination, an operation not possible with an existing Petri dish.

The container in accordance with the invention may be employed in all microbiological test methods utilizing a microporous membrane filter and in particular the process which is the subject matter of pending U.S. patent application No. 691,687 filed Jan. 15, 1985.

Other aspects and advantages of the invention will now be further described with reference to the appended drawings.

DESCRIPTION OF THE PREFERRED EMBODIMENTS

Figure 1:
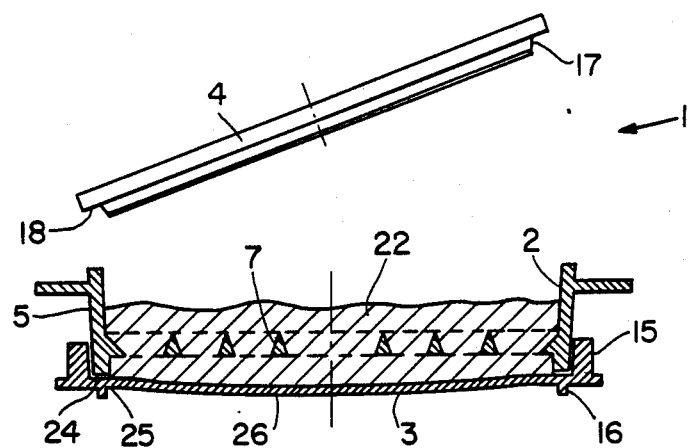
FIG. 1 is a view in cross-section of a first embodiment of a container in accordance with the present invention, in position of filling with nutrient medium.

Referring to the drawings and FIG. 1 in particular, a container 1 in accordance with the present invention is shown inverted and includes three primary parts, a cylindrical casing 2, a lid 3 and a base 4. The casing has a single wall 5 which is slightly frustoconical to enable a liquid-tight fit between the two ends of the casing and the lid and base, respectively.

Near the upper end of the casing 2 (lower end as shown in FIG. 1), the wall 5 has attached to it a perforated support grid 7 designed to support a culture medium and which has a flat circular shape coaxial with the casing 2. This grid, the circular edge of which is attached to the wall 5 of the casing, may be in the form of an array of concentric circular elements 8 and radial elements 9 (see FIG. 6). The top surface of the grid, that is the surface facing the lid 3, is preferably flat, while the elements 8 and 9 may have a triangular transverse cross-section. A grid of this shape more readily retains the gel culture medium when the container is in its normal position for use as a Petri dish, i.e., upside down relative to the position shown in FIG. 1.

The upper end of the casing 2 has a flat annular surface 24 lying in a plane perpendicular to the axis of the casing. The casing also includes handling members, specifically two handling lugs 13 and 14, located in diametrically opposed positions (see FIG. 6).

The lid 3 is of circular shape and defines an upper surface in on piece at the edge having a shallow, substantially cylindrical rim 15 which is preferably slightly frustoconical to enable it to be fitted in a liquid-tight manner over the open upper end of the casing 2. As shown in FIGS. 1 through 5, the lid may be in the form of a circular member defining a flat annulus 25 cooperating with the flat surface 24 of the casing and a central inner surface 26 which is slightly concave on the side facing the casing. The other side being convex is preferably provided with a cylindrical stand 16 of smaller diameter than the lid which supports the container when it is turned upside down. The stand thus compensates for the convex shape of the other side of the lid. The concave shape of the lid 3 is of particular benefit in that it enables the surface of the nutrient medium which is brought into contact with the micro-organisms to be molded with a convex shape.

Like the lid 3, the base 4 is a circular member defining a flat surface in one piece at its edge with a shallow, substantially cylindrical rim 17. This rim is also preferably slightly frustoconical to enable it to be fitted in a liquid-tight way to the open lower end of the casing 2. The rim 17 may incorporate a step 18 to facilitate grasping the base 4 when it is removed from the casing. Both the lid and the base may each include handling members (not shown) to facilitate fitting them in a liquid-tight way onto the casing.

The structure described above facilitates the filling of the container with a culture medium that enables it to effectively function as a micro-organism growth device in a manner heretofore not possible. Filling is accomplished by resting the container 1 upside down on its liquid-tight lid 3 on the stand 16, removing the base 4 and pouring the culture medium into the casing 2, which is fitted only with its lid. Medium is added up to the point where the perforated support grid 7 is immersed in the medium. The base is then replaced and the container, which may be stored in a refrigerator for subsequent use, is turned over so as to rest on its base, with the cover on its top, ready for use. In this manner, the surface of the nutrient medium which is brought into contact with the micro-organisms is not the top surface resulting from the pouring operation. Instead, because the container is turned over, the bottom surface of the poured medium which is directly in contact with the lid becomes the surface of interest with respect to contact with the membrane filter. Since this "contact" surface of the medium is molded according to the shape of the lid, it does not have any of the defects mentioned previously.

Figure 2:
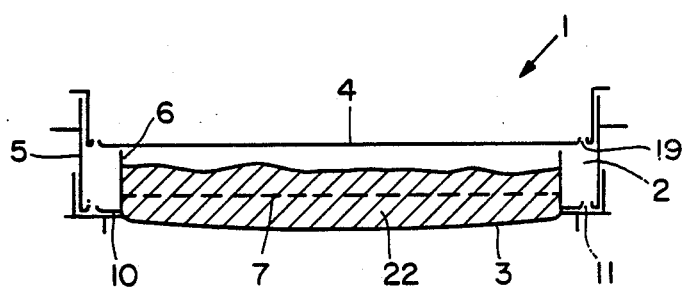
FIG. 2 is a schematic representation of a second embodiment of the container in accordance with the invention, in position for filling with nutrient medium.

The embodiment shown schematically in FIG. 2 differs from that shown in FIG. 1 in that the casing 2 comprises two concentric and substantially cylindrical walls 5 and 6 instead of a single wall 5. In this second embodiment, which is specifically designed for use with apparatus of the type which is the subject matter of the previously mentioned U.S. patent application No. 691,687, the outer wall 5 is slightly frustoconical to enable, as in the FIG. 1 embodiment, liquid-tight fitting of the two open ends of the casing with the lid 3 and the base 4, respectively. The inside wall 6 and the perforated support grid 7 form an integral, one piece unit.

The two concentric walls 5 and 6 are joined at their upper end by a flat annulus 10 coaxial with the casing. The annulus 10 comprises a number of axial perforations 22, four of which are shown in FIG. 6, which are preferably located in a circular groove 12 on the upper surface of the annulus 10.

In this second embodiment the base 4 has near its edge and inward from the rim 17 axial perforations 19 which serve as vents. These vents are preferably situated on the same vertical line as the annulus 10 joining the two concentric walls 5 and 6 of the casing. This structure provides communication between the space defined by these two walls and the external environment thereby preventing any piston-type interaction between the base 4 and the casing 2 of the container.

Figure 3:
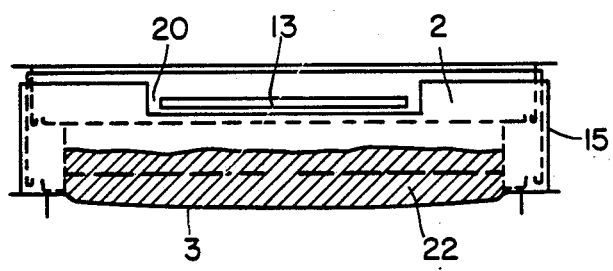
FIG. 3 is a schematic representation of another embodiment of the container in accordance with the invention in position analogous to that of FIG. 1.
Figure 4:
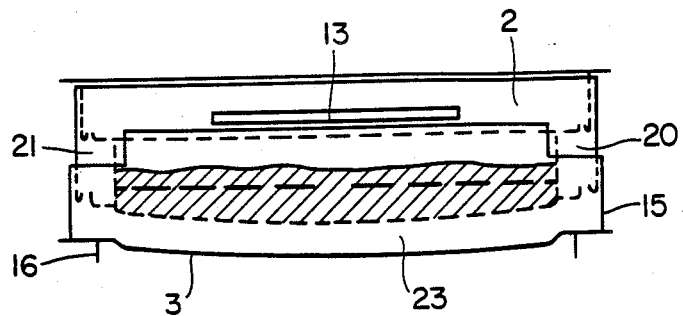
FIG. 4 shows the same embodiment as FIG. 3 but with the lid rotated 90° relative to the position shown in FIG. 3.

A third embodiment shown in FIGS. 3 and 4 differs from those shown in FIGS. 1 and 2 in terms of the shape of the lid 3. In this embodiment, the lid 3 has a rim 15 which is substantially longer in the axial direction than the rim of the previous embodiments and which includes two diametrically opposed notches 20 and 21 on the side opposite the cylindrical stand 16. These notches in the lid cooperate with the handling lugs 13 and 14 on the casing 2 to hold these two parts (i.e. lid and casing) nested one within the other either to a maximum depth, in which position the culture medium 22 is in contact with the lid 3 as shown in FIG. 3, or, following a 90° rotation of the lid relative to the casing, to a lesser depth, leaving an incubation chamber 23 between the culture medium and the lid, as shown in FIG. 4.

Figure 5:
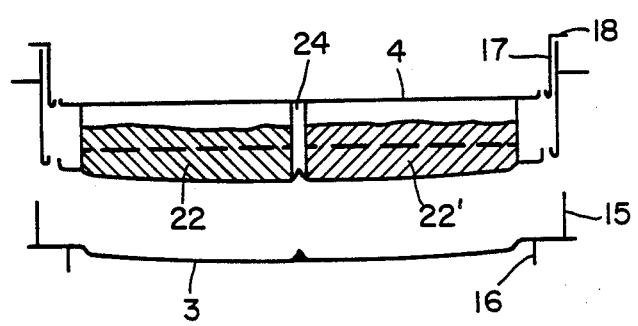
FIG. 5 is a schematic representation of another embodiment of the invention.
Figure 6:
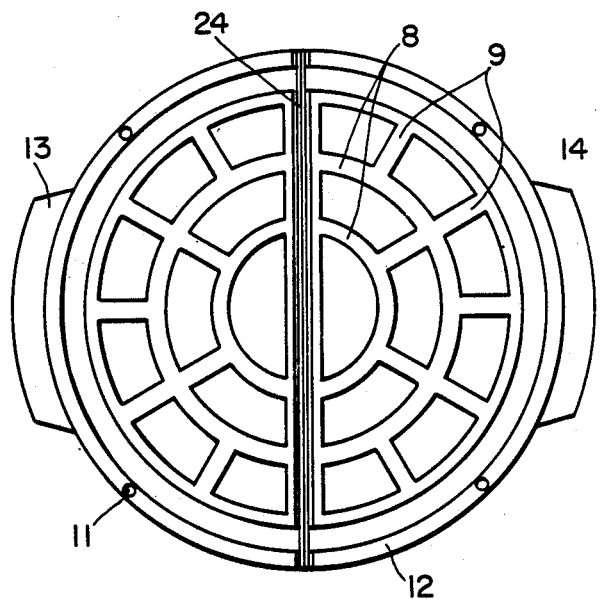
FIG. 6 is a plan view of the cylindrical casing for the embodiment shown in FIG. 5.

A fourth embodiment shown in FIGS. 5 and 6 differs from those described previously in that the casing 4 includes a liquid-tight barrier 24, so that it can contain two different culture mediums 22 and 22'.

It will be obvious that the container in accordance with the present invention, given the advantages that it provides, is particularly beneficial in numerous applications. Such a container is usable not only as a Petri dish but also for checking microbiological contamination of surfaces. The container is well suited to the biological testing method and device using a sleeve as described in previously mentioned U.S. patent application No. 691,687. Finally, the container is able to house one or more culture mediums to provide for counting different micro-organisms captured on the same microporous membrane filter, thereby reducing the testing time and the amount of equipment to be used, and consequently the cost of the test.

Although several embodiments of the invention have been described in detail above, this is merely for illustration. Accordingly the present invention is intended to be limited only by the appended claims.

What is claimed:

1. A container constructed to receive a culture medium for micro-organisms, comprising: a substantially cylindrical casing completely open at both ends, wherein said casing comprises concentric and substantially cylindrical inner and outer walls and said inner wall is integrally joined with a transverse perforated support grid, and further comprising an annulus joining said inner and outer walls, a plurality of axial perforations through said annulus, said transverse perforated support grid having a circular edge joined to said inside wall of said casing at a position intermediate said ends, a base and a lid, said casing having a frusto-conical shape, and said base and said lid having a frusto-conical shape corresponding to that of said casing such that said base and said lid are constructed to fit in a liquid-tight manner onto each of the respective ends of said casing whereby a liquified culture medium can be poured into said container while it is resting upside down on said lid with said base removed such that said medium directly contacts said lid.

2. A container according to claim 1, wherein one end of said casing has a flat annular surface perpendicular to the axis of said casing and said lid has a complementary flat surface constructed to cooperate with said flat annular surface on said casing to secure said liquid-tight fit of said lid to casing.

3. A container according to claim 1, wherein said lid is circular, has at its edge an integral, substantially cylindrical rim and defines a flat annulus cooperating with one end of said casing and a central inside surface facing said casing which is concave.

4. A container according to claim 3, wherein said lid comprises on the side opposite said rim at stand of smaller diameter constructed to serve as a support when said container is placed upside down on its lid.

5. A container according to claim 1, wherein said base is circular, defines a flat surface and has at its edge an integral, substantially cylindrical rim.

6. A container according to claim 5, wherein said rim comprises a step constructed to limit the relative positioning of said casing and said base one within the other.

7. A container according to claim 11, wherein said annulus has an upper surface in which is formed a circular groove containing said axial perforations.

8. A container according to claim 1, including handling member means forming part of either of said casing, base or lid.

9. A container according to claim 1, wherein said perforated support grid comprises an array of radial and concentric circular elements.

10. A container according to claim 9, wherein said elements have a flat upper surface.

11. A container according to claim 9, wherein said elements have a triangular cross-section.

12. A container according to claim 3, wherein said casing comprises handling lugs in diametrally opposed relationship to each other and a substantially cylindrical rim on said lid has two notches in diametrally opposed relationship constructed to receive said lugs in two different positions at two different depths by virtue of 90° rotation of said lid relative to said casing.

13. A container according to claim 8 wherein said handling member means form part of said casing, base and lid.

14. A method of detecting micro-organisms comprising the steps of: (a) providing a container having a substantially cylindrical or frustoconical casing completely open at both ends, a transverse perforated support grid having a circular edge joined to an inside wall of said casing, said casing comprises concentric and substantially cylindrical inner and outer walls and said inner wall is integrally joined with said perforated support grid and further comprising a flat annulus joining said inner and outer walls, a plurality of axial perforations through said annulus, a base and a lid which fits in a liquid-tight way onto an upper end of said casing (b) pouring a culture medium at a raised temperature into said container while it is resting upside down on said lid with said base removed, (c) fitting said base to said casing, (d) resting said container on said base and removing said lid from said casing to enable the surface of said culture medium previously in contact with said lid to be used to receive micro-organisms whose presence is to be detected.

* * * * *